United States Patent

Spagnol et al.

[11] Patent Number: 5,817,878
[45] Date of Patent: Oct. 6, 1998

[54] PROCESS FOR THE ACYLATION OF AROMATIC ETHERS

[75] Inventors: Michel Spagnol, Lyons; Laurent Gilbert, Paris; Eric Benazzi, Montesson; Christian Marcilly, Houilles, all of France

[73] Assignee: Rhone-Poulenc Chimie, Courbevoie, France

[21] Appl. No.: 765,537

[22] PCT Filed: May 10, 1996

[86] PCT No.: PCT/FR96/00717

§ 371 Date: Jan. 9, 1997

§ 102(e) Date: Jan. 9, 1997

[87] PCT Pub. No.: WO96/35656

PCT Pub. Date: Nov. 14, 1996

[30] Foreign Application Priority Data

May 12, 1995 [FR] France .................................. 95 05683

[51] Int. Cl.⁶ .................................................. C07C 45/45
[52] U.S. Cl. ............................ 568/319; 568/322; 549/436
[58] Field of Search .................... 568/319, 322, 568/222; 549/436

[56] References Cited

U.S. PATENT DOCUMENTS

| | | |
|---|---|---|
| 3,308,069 | 3/1967 | Wadlinger ............................... 252/455 |
| 4,960,943 | 10/1990 | Botta ....................................... 568/319 |
| 5,200,168 | 4/1993 | Apelian ................................... 423/714 |
| 5,227,529 | 7/1993 | Neuber ................................... 568/319 |
| 5,310,534 | 5/1994 | Fajula ..................................... 423/715 |
| 5,434,310 | 7/1995 | Waldman et al. ..................... 568/319 |
| 5,637,773 | 6/1997 | Desmurs et al. ...................... 568/319 |

FOREIGN PATENT DOCUMENTS

| | | | |
|---|---|---|---|
| 0 455 332 | 3/1991 | European Pat. Off. ........ C07C 45/46 |
| 2667063 | 9/1990 | France ......................... C07C 49/813 |

*Primary Examiner*—James H. Reamer
*Attorney, Agent, or Firm*—Katherine L. Carleton; Jean-Louis Seugnet

[57] ABSTRACT

The present invention concerns a process for the acylation of an aromatic ether.

Preferably, the invention relates to a process for the acylation of an unsubstituted aromatic ether, in particular anisole.

The acylation process of the invention consists of reacting the ether with an acylation agent in the presence of a zeolitic catalyst, and is characterized in that the acylation reaction is carried out in the presence of an effective quantity of a catalyst comprising a beta zeolite with an atomic ratio denoted "global Si/Me$^1$" between the number of atoms of the element silicon and the number of atoms of every trivalent element Me$^1$ contained in the zeolite of no less than 15, preferably in the range 15 to 55, and more preferably in the range 18 to 35.

27 Claims, No Drawings

PROCESS FOR THE ACYLATION OF AROMATIC ETHERS

This application is A371 of PCT/FR 96/00717.

The present invention concerns a process for the acylation of an aromatic ether.

Preferably, the invention relates to a process for the acylation of an unsubstituted aromatic ether, more particularly anisole.

The invention is applicable to the preparation of alkoxyaromatic alkylketones.

Conventional processes for the acylation of aromatic compounds, in particular the ethers of phenols, consist of carrying out a Friedel-Crafts acylation reaction.

The aromatic compound is reacted with an acylation agent in the presence of a catalyst which is generally aluminium chloride.

This type of process is illustrated by the work of C KURODA et al., [Sci. Papers Inst. Phys. Chem. Res. 18, pp 51–60 (1932)] which describes the preparation of methoxy-acetophenones by the reaction of an aromatic compound carrying 1 to 3 methoxy groups with acetyl chloride in the presence of aluminium chloride.

The use of aluminium chloride, however, has a number of disadvantages. Aluminium chloride is corrosive and an irritant. Further, a large quantity of aluminium chloride must be used, at least equal to the stoichiometric quantity, because of complexation with the ketone formed. As a result, the aluminium chloride is not a true catalyst.

At the end of the reaction, the aluminium chloride must be eliminated from the reaction medium by carrying out acidic or basic hydrolysis.

Hydrolysis implies the addition of water to the reaction medium, considerably complicating the process since the metal cation, and more particularly the aluminium cation, forms aluminium polyoxo- and/or polyhydroxo complexes of milky consistency, which are difficult to separate. This necessitates a long, expensive treatment following hydrolysis comprising extraction of the organic phase, separation of the aqueous and organic phases, and even drying of the latter. Separation of aluminium chloride is thus lengthy and expensive.

Further, there are problems with aqueous saline effluents which must then be neutralised and which necessitate an additional operation.

Still further, the aluminium chloride cannot be recycled as it has been hydrolysed.

In order to overcome this disadvantage, it has been suggested that the reaction be carried out in the presence of heterogeneous catalysts.

Thus for about a decade, zeolites have been recommended for use as acylation catalysts.

Prins et al. described the acetylation of anisole by acetic anhydride [9$^{th}$ International Zeolite Congress—Montréal Congrès (1992)] in the presence of zeolites such as β zeolite or USY zeolite. It should be noted that β zeolites produced more interesting results as regards both the degree of conversion and the reaction yield.

However, the catalyst performances described were not satisfactory. The use of that catalyst on an industrial scale causes problems since the productivity of the catalyst is insufficient necessitating a very large reactor.

An object of the present invention is to provide a process which can overcome the above disadvantages.

We have now discovered, and this constitutes an object of the present invention, a process for the acylation of an aromatic ether which consists of reacting the ether with an acylation agent in the presence of a zeolitic catalyst, the process being characterized in that the acylation reaction is carried out in the presence of an effective quantity of a catalyst comprising a beta zeolite with an atomic ratio denoted "global Si/Me$^1$" between the number of atoms of the element silicon and the number of atoms of every trivalent element Me$^1$ contained in the zeolite of no less than 15, preferably in the range 15 to 55, and more preferably in the range 18 to 35.

The term Me$^1$ denotes any element with a degree of oxidation of +3, in particular aluminium, gallium, iron, boron and mixtures thereof, preferably aluminium.

The "global Si/Me$^1$" atomic ratio of the zeolite is primarily determined by X ray fluorescence.

The catalyst used in the process of the invention comprises an active phase which is a beta (β) zeolite of structural type BEA which has certain well defined characteristics. It has a low concentration of element Me$^t$, which is preferably aluminium.

More precisely, in its dehydrated state the zeolite has a chemical composition which corresponds to the following empirical formula:

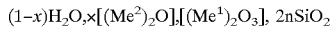

where:

Me$^1$ denotes any element with a degree of oxidation of +3, preferably aluminium, gallium, iron, boron and mixtures thereof;

Me$^2$ denotes a metal selected from the group of elements in column 1a and mixtures thereof, preferably alkali metals such as lithium, sodium, potassium, rubidium and caesium;

n, equal to the "global Si/Me$^1$" atomic ratio defined above, is in the range 15 to 55, preferably in the range 18 to 35;

x, equal to the atomic ratio Me$^2$/Me$^1$ between the number of atoms of alkali metal Me$^2$ and the number of atoms of every trivalent element Me$^1$ of the zeolite, is in the range 0 to 0.2, preferably in the range 0.005 to 0.1.

The term "Me$^2$" denotes a metal selected from the group of elements in column 1a and mixtures thereof, preferably alkali metals such as lithium, sodium, potassium, rubidium and caesium. Me$^2$ preferably represents sodium or potassium.

Reference should be made to the periodic classification of the elements published in the "Bulletin de la Société Chimique de France", No 1 (1966) for the definition of the elements.

Beta zeolites are described in the literature [see "Atlas of Zeolite Structure Types" by W. M. Meier and D. H. Olson, published by the Structure Commission of the International Zeolite Association (1978), or U.S. Pat. No. 3,308,069, or the article by P. Caullet et al., Zeolites 12, pp. 240 (1992)].

They can be synthesised in a conventional basic medium or in a fluoride medium as described in French patent FR-A-2 653 347.

In order to use a β zeolite with the above characteristics, it may be necessary to dealuminise the zeolite so that the "global Si/Me$^1$" atomic ratio defined above is in the prescribed ranges.

Methods which are known to the skilled person can be used, non exhaustive examples of which are: calcining in the presence of vapour, calcining in the presence of steam followed by attack with mineral acids (HNO$_3$, HCl . . . ), direct dealuminising using reactants such as silicon tetrachloride (SiCl$_4$), ammonium hexafluorosilicate ((NH$_4$)

$_2SiF_6$), or ethylenediaminetetraacetic acid (EDTA) or its mono- or disodium form. Dealuminising can also be carried out by direct acid attack with solutions of mineral acids such as hydrochloric acid, nitric acid, sulphuric acid or organic actids, in particular acetic acid or oxalic acid.

Any combination of the above dealuminising methods is also possible.

The zeolite constitutes the catalytic phase. It can be used alone or mixed with a mineral matrix. In this description, the term "catalyst" is used to denote a catalyst formed entirely of zeolite or mixed with a matrix prepared using techniques which are known to the skilled person.

The matrix can be selected from metal oxides such as aluminium oxides, silicon oxides and/or zirconium oxides, or from clays, in particular kaolin, talc or montmorillonite.

The active phase in the catalyst represents 5% to 100% by weight of the catalyst.

The catalysts can be in different forms in the process of the invention: powder, formed products such as granules (for example extrudates or spherules) or pellets, obtained by extrusions moulding, compacting or any other known process. Granules or spherules are used industrially as they have the most advantages as regards both efficiency and ease of use.

As mentioned above, the process of the invention is suitable for carrying out the acylation of an aromatic ether, preferably an unsubstituted aromatic ether.

In the following disclosure of the present invention, the term "aromatic ether" denotes an aromatic compound in which a hydrogen atom which is directly bonded to the aromatic nucleus is replaced by an ether group and the term "aromatic" denotes the conventional idea of aromaticity as defined in the literature, in particular Jerry MARCH, Advanced Organic Chemistry, $4^{th}$ edition, John Wiley and Sons. 1992, pp.40 ff.

The term "substituted aromatic ether" denotes an aromatic ether containing at least one other substituent on the aromatic nucleus, preferably in the ortho position.

More precisely, the present invention provides a process for the acylation of an aromatic ether with general formula (I):

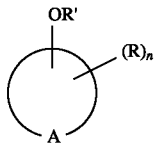

where:

A represents the residue of a cycle forming all or a portion of a monocyclic or polycyclic aromatic carbocyclic system containing at least one OR' group: the cyclic residue may carry one or more substituents;

R represents one or more substituents which may be identical or different;

R' represents a hydrocarbon radical containing 1 to 24 carbon atoms, which may be a saturated or unsaturated, linear or branched acyclic aliphatic radical; a monocyclic or polycyclic, and saturated, unsaturated or aromatic cycloaliphatic radical; or a saturated or unsaturated, linear or branched aliphatic radical carrying a cyclic substitutent;

R' and R may form a cycle which may contain a further heteroatom;

n is a number less than or equal to 4.

For simplicity in the present text, the term "alkoxy groups" denotes R'—O— type groups where R' has the meaning given above. R' thus represents both a saturated, unsaturated or aromatic, acyclic or cycloaliphatic aliphatic radical and a saturated or unsaturated aliphatic radical carrying a cyclic substitutent.

The aromatic ether used in the process of the invention has formula (I) where R' represents a saturated or unsaturated, linear or branched acyclic aliphatic radical.

More preferably, R' represents a linear or branched alkyl radical containing 1 to 12 carbon atoms, preferably 1 to 6 carbon atoms: the hydrocarbon chain may be interrupted by a heteroatom (for example oxygen), by a functional group (for example —CO—) and/or may carry a substitutent (for example a halogen).

The saturated or unsaturated, linear or branched acyclic aliphatic radical may carry a cyclic substitutent. The term cycle preferably denotes a saturated, unsaturated or aromatic carbocyclic cycle, preferably cycloaliphatic or aromatic, and in particular cycloaliphatic containing 6 carbon atoms in the cycle, or benzenic.

The acyclic aliphatic radical may be bonded to the cycle by a valence bond, a heteroatom or a functional group; examples are given above.

The cycle may optionally be substituted; examples of cyclic substituents are substituents such as R whose meaning is described for formula (Ia).

R' may also represent a carbocyclic radical which is saturated or contains 1 or 2 unsaturations in the cycle, generally containing 3 to 7 carbon atoms, preferably 6 carbon atoms in the cycle; the cycle may be substituted with substituents such as R.

R' may also represent an aromatic carbocyclic radical, preferably a monocyclic radical generally containing at least 4 carbon atoms, preferably 6 carbon atoms in the cycle; the cycle may be substituted with substituents such as R.

The process of the invention is particularly applicable to aromatic ethers with formula (I) where R' represents a linear or branched alkyl radical containing 1 to 4 carbon atoms or a phenyl radical.

Examples of preferred radicals R' of the invention are methyl and ethyl radicals.

In general formula (I) for aromatic ethers, residue A may represent the residue of a monocyclic aromatic carbocyclic compound containing at least 4 carbon atoms, preferably 6 carbon atoms, or the residue of a polycyclic carbocyclic compound which may be constituted by at least 2 aromatic carbocycles and form between them ortho- or ortho- and pericondensed systems or by at least 2 carbocycles of which at least one is aromatic and forming between them ortho- or ortho- and pericondensed systems. A particular example is a naphthalenic residue.

Residue A may carry one or more substituents on the aromatic nucleus.

Examples of substituents R are given below, but this list is not limiting. Any substituent can be present on the cycle provided that it does not interfere with production of the desired product.

The process of the invention is particularly applicable to aromatic ethers with formula (Ia):

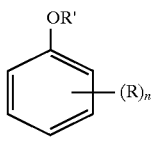

where:

n is a number less than or equal to 4, preferably 0 or 1;

radical R' represents a linear or branched alkyl radical containing 1 to 6 carbon atoms, preferably 1 to 4 carbon atoms, such as methyl, ethyl, propyl, isopropyl, butyl, isobutyl, sec-butyl, tert-butyl or a phenyl radical;

radical(s) R represent one of the following atoms or groups:
- a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;
- a linear or branched alkenyl radical containing 2 to 6 carbon atoms, preferably 2 to 4 carbon atoms, such as vinyl, allyl;
- a cyclohexyl or benzyl radical;
- a linear or branched alkoxy radical containing 1 to 6 carbon atoms, preferably 1 to 4 carbon atoms, such as a methoxy, ethoxy, propoxy, isopropoxy or butoxy radical;
- an acyl group containing 2 to 6 carbon atoms;
- a radical with formula:
    —$R_1$—OH
    —$R_1$—COO$R_2$
    —$R_1$—CHO
    —$R_1$—NO$_2$
    —$R_1$—CN
    —$R_1$—N—($R_2$)$_2$
    —$R_1$—CO—N—($R_2$)$_2$
    —$R_1$—X
    —$R_1$—CF$_3$
  where $R_1$ represents a valence bond or a saturated or unsaturated, linear or branched divalent hydrocarbon radical containing 1 to 6 carbon atoms such as methylene, ethylene, propylene, isopropylene, or isopropylidene; $R_2$ represents a hydrogen atom or a linear or branched alkyl radical containing 1 to 6 carbon atoms; and X represents a halogen atom, preferably a chorine, bromine or fluorine atom, radicals R' and R and the 2 successive atoms of the benzene ring may form between then a cycle containing 5 to 7 carbon atoms, which may contain a further heteroatom.

When n is greater than or equal to 1, radicals R' and R and the 2 successive atoms of the benzene ring can be bonded together by an alkylene, alkenylene or alkenylidene radical containing 2 to 4 carbon atoms to form a saturated, unsaturated or aromatic heterocycle containing 5 to 7 carbon atoms. One or more carbon atoms may be replaced by a further heteroatom, preferably oxygen. Thus radicals OR' and R may represent a dioxymethylene or a dioxyethylene radical.

In formula (Ia), R' preferably represents a linear or branched alkyl radical containing 1 to 4 carbon atoms, preferably a methyl or ethyl radical.

The aromatic ether with formula (I) may carry one or more R substituents.

More preferably, R represents one of the following atoms or groups:
- a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;
- a linear or branched alkoxy radical containing 1 to 6 carbon atoms, preferably 1 to 4 carbon atoms, such as a methoxy, ethoxy, propoxy, isopropoxy, butoxy, isobutoxy, sec-butoxy or tert-butoxy radical;
- a halogen atom, preferably a fluorine, chlorine or bromine atom, or a trifluoromethyl radical.

In formula (Ia), R preferably represents a linear or branched alkoxy radical containing 1 to 4 carbon atoms, preferably a methoxy or ethoxy radical.

The process of the invention is particularly applicable to aromatic ethers with formula (I) or (Ia) where:
- n is equal to 0 or 1;
- R' represents a linear or branched alkyl radical containing 1 to 6 carbon atoms or a phenyl radical;
- R represents a linear or branched alkoxy radical containing 1 to 4 carbon atoms, preferably a methoxy or ethoxy radical;
- radicals OR' and R form a dioxymethylene or dioxyethylene radical.

More particularly, the process of the invention is applicable to unsubstituted aromatic ethers with formula (I) or (Ia) where n equals 0: R' preferably represents a linear or branched alkyl radical containing 1 to 6 carbon atoms, preferably 1 to 4 carbon atoms, such as methyl, ethyl, propyl, isopropyl, butyl, isobutyl, sec-butyl, tert-butyl, or a phenyl radical.

It is particularly suitable for aromatic ethers with formula (Ia) where radical R' is an alkyl radical, preferably methyl or ethyl.

Particular illustrations of compounds with formula (I) are:
- unsubstituted monoethers such as anisole, ethoxybenzene (phenetole), propoxybenzene, isopropoxybenzene, butoxybenzene, isobutoxybenzene, 1-methoxynaphthalene, 2-methoxynaphthalene, 2-ethoxynaphthalene; substituted monoethers such as 2-chloroanisole. 3-clhloroanisole, 2-bromoanisole. 3-bromoanisole, 2-methylanisole, 3-methylanisole, 2-ethylanisole, 3-ethylanisole, 2-isopropylanisole, 3-isopropylanisole, 2-propylanisole, 3-propylanisole, 2-allylanisole, 2-butylanisole, 3-butylanisole, 2-benzylanisole, 2-cyclohexylanisole, 1-bromo-2-ethoxybenzene, 1-bromo-3-ethoxybenzene, 1-chloro-2-ethoxybenzene, 1-chloro-3-ethoxybenzene, 1-ethoxy-2-ethylbenzene, 1-ethoxy-3-ethylbenzene, 1-methoxy-2-allyloxybenzene, 2,3-dimethylanisole, and 2,5-dimethylanisole;
- diethers such as veratrol, 1,3-dimethoxybenzene, 1,4dimethoxybenzene, 1,2-diethoxybenzene, 1,3-diethoxybenzene, 1,2dipropoxybenzene, 1,3-dipropoxybenzene, 1,3-dipropoxybenzene, 1,2-methylenedioxybenzene, and 1,2-ethylenedioxybenzene;
- triethers such as 1,2,3-trimethoxybenzene, 1,3,5-trimethoxybenzene and 1,3,5-triethoxybenzene.

The compounds for which the process of the invention is particularly applicable are unsubstituted ethers, preferably with formula (I) or (Ia) where n equals 0. The invention is well suited to the acylation of anisole.

The acylation reactant is selected from the group formed by carboxylic acid halides and carboxylic acid anhydrides.

The carboxylic acids are saturated or unsaturated, linear or branched aliphatic carboxylic acids or saturated or unsaturated cycloaliphatic acids which may be substituted.

In particular, they have the following formula (II):

where:
$R_3$ represents:
- a saturated or unsaturated, linear or branched aliphatic radical containing 1 to 24 carbon atoms; or a saturated or unsaturated, monocyclic or polycyclic cycloaliphatic radical containing 3 to 12 carbon atoms;

X' represents:
  a halogen atom, preferably a chlorine or bromine atom;
  a —O—CO—$R_1$ radical where $R_1$, which may be identical or different to $R_3$, has the same meaning as $R_3$; $R_3$ and $R_4$ may together form a saturated or unsaturated, linear or branched aliphatic radical containing at least 2 carbon atoms.

More preferably, $R_3$ represents a linear or branched alkyl radical containing 1 to 12 carbon atoms, preferably 1 to 6 carbon atoms: the hydrocarbon chain may be interrupted by a heteroatom (for example oxygen), a functional group (for example —CO—) and/or may carry substituents (for example halogen atoms or a $CF_3$ group).

$R_3$ also represents an alkenyl radical containing 2 to 10 carbon atoms, such as vinyl, propenyl, butenyl, pentenyl, hexenyl, octenyl or decenyl.

Radical $R_3$ also represents a non aromatic radical, preferably a cycloaliphatic radical, for example a cyclohexyl radical, which may be substituted. Any substitutent can be present on the cycle provided that it does not interfere with production of the desired product.

Particular examples of substituents are:
  a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;
  a linear or branched alkoxy radical containing 1 to 6 carbon atoms, preferably 1 to 4 carbon atoms, such as a methoxy, ethoxy, propoxy, isopropoxy, butoxy, isobutoxy, sec-butoxy or tert-butoxy radical;
  a hydroxy group;
  a halogen atom, preferably a fluorine, chlorine or bromine atom.

Preferred acylation agents are acid anhydrides. In particular, they have formula (II) where $R_3$ and $R_4$ are identical and represent an alkyl radical containing 1 to 4 carbon atoms, which may carry halogen atoms, preferably chlorine.

When the acylation agent is an acid halide, it preferably has formula (II) where X' represents a chlorine atom and $R_3$ represents an alkyl radical containing 1 to 4 carbon atoms, preferably methyl or ethyl, and may carry halogen atoms, preferably chlorine.

Particular illustrative examples of acylation agents with formula (II) are:
  acetic anhydride;
  propanoic anhydride;
  isobutyric anhydride;
  trifluoroacetic anhydride;
  monochloroacetyl anhydride;
  dichloroacetyl anhydride;
  acetyl chloride;
  monochloroacetyl chloride;
  dichloroacetyl chloride;
  propanoyl chloride;
  isobutanoyl chloride;
  pivaloyl chloride:
  crotonyl chloride.

In accordance with the invention, the acylation reaction is advantageously carried out in the liquid phase comprising the aromatic ether and the acylation agent in the presence of catalyst.

One of the starting reactants can act as the reaction solvent, but it is also possible to use an organic solvent.

Particular examples of suitable solvents are aliphatic or aromatic hydrocarbons which may or may not be halogenated, aliphatic, cycloaliphatic or aromatic ether-oxides, or polar aprotic solvents.

Particular examples of aliphatic or cycloaliphatic hydrocarbons are paraffins, in particular hexane, heptane, octane, nonane, decane, undecane, dodecane, tetradecane or cyclohexane, and aromatic hydrocarbons, in particular benzene, toluene, xylenes, cumene, and petroleum cuts constituted by a mixture of alkylbenzenes, in particular Solvesso® type cuts.

Particular examples of aliphatic or aromatic halogenated hydrocarbons are a perchlorinated hydrocarbons, in particular tetrachloroethylene, hexachloroethane; partially chlorinated hydrocarbons such as dichloromethane, chloroform, 1,2-dichloroethane, 1,1,1-trichloroethane, 1,1,2,2-tetrachloroethane, pentachloroethane, trichloroethylene, 1-chlorobutane, 1,2-dichlorobutane; monochlorobenzene, 1,2-dichlorobenzene, 1,3-dichlorobenzene, 1,4-dichlorobenzene, 1,2,4-trichlorobenzene or mixtures of different chlorobenzenes; bromoform, bromoethane or 1,2-dibromoethane; monobromobenzene or mixtures of monobromobenzene with one or more dibromobenzenes; and 1-bromonaphthalene.

Aliphatic, cycloaliphatic or aromatic ether-oxides can also be used as organic solvents, more particularly diethyl oxide, dipropyl oxide, diisopropyl oxide, dibutyl oxide, methyltertiobutylether, dipentyl oxide, diisopentyl oxide, ethyleneglycol dimethyl ether (1,2-dimethoxyethane), diethyleneglycol dimethylether (1.5-dimethoxy-3-oxapentane); biphenyl oxide or benzyl oxide; dioxane, and tetrahydrofuran (THF).

Particular examples of polar aprotic solvents which can also be used in the process of the invention are linear or cyclic carboxamides such as N,N-dimethylacetamide (DMAC), N,N-diethylacetamide, dimethylformamide (DMF), diethylformamide or 1-methyl-2-pyrrolidinone (NMP); dimethylsulphoxide (DMSO); cyclic or non cyclic sulphones such as tetramethylsulphone, or dimethylsulphone; hexamethlylphosphotriamide (HMPT). and cyclic or non cyclic tetrasubstituted ureas such as dimethylethyleneurea, dimethylpropyleneurea, and tetramethylurea.

Preferred solvents are: dichloromethane, tetrachloromethane, THF and diethyl oxide.

A mixture of organic solvents can also be used.

Preferably, the starting substrate is used as the reaction solvent.

As mentioned above, the aromatic ether is reacted with an acylation agent, optionally in the presence of a reaction solvent as defined above and in the presence of a solid catalyst as defined above.

The ratio between the number of moles of aromatic ether and the number of moles of acylation agent can vary since the substrate may act as the reaction solvent. Thus the ratio can be between 0.1 and 20, preferably between 0.5 and 10.

The quantity of catalyst used can vary between wide limits.

When the process is carried out batchwise, the catalyst can represent 0.01% to 50% by weight, preferably 1.0% to 20%, by weight with respect to the aromatic ether used. When the process is carried out continuously, however, for example by reacting a mixture of aromatic ether and acylation agent on a fixed catalyst bed, catalyst/aromatic ether ratios do not make sense and at a given instant, there may be an excess by weight of catalyst with respect to the starting aromatic ether.

The quantity of organic solvent used is generally selected so that the ratio between the number of moles of organic solvent and the number of moles of aromatic ether preferably varies between 0 and 100, more preferably between 0 and 50.

It is also possible to carry out the process of the invention in the presence of water: this latter can represent 0% to 10% by weight of acylation agent.

The temperature at which the acylation reaction is carried out depends on the reactivity of the starting substrate and that of the acylation agent.

It is between 20° C. and 300° C., preferably between 40° C. and 200° C.

The reaction is generally carried out at atmospheric pressure but lower pressures or higher pressures may also be suitable. The pressure is autogenous when the reaction temperature is higher than the boiling point of the reactants and/or products.

The process can be carried out batchwise or continuously.

In the first variation, there are no constraints on using the reactants. They can be introduced in any order.

After bringing the reactants into contact, the reaction mixture is brought to the desired temperature.

In the other variation, the reaction is carried out continuously in a tube reactor comprising the solid catalyst disposed in a fixed bed.

The aromatic ether and the acylation agent can be introduced into the reactor separately or as a mixture.

They can also be introduced in a solvent as mentioned above.

The residence time for the material stream on the catalytic bed varies, for example, between 15 minutes and 10 hours, preferably between 30 minutes and 5 hours.

At the end of the reaction, a liquid phase is obtained comprising the acylated aromatic ether which can be recovered conventionally, by distillation or recrystallisation from a suitable solvent, after elimination of excess reactants.

The process of the invention is particularly suitable for the preparation of 4-methoxyacetophenone, known as acetoanisole, by the acetylation of anisole.

One advantage of the process of the invention is that the acylation reaction takes place without O-dealkylation of the starting aromatic ether.

The following examples illustrate the invention without in any way limiting its scope.

Examples 1 and 2 relate to the preparation of zeolites which are used in Examples 3, 4, and 6 to 8.

Examples 5 and 9 are comparative examples.

The yields given in the examples are defined as follows:

$$\text{Yield: } RR_{AA} = \frac{\text{number of moles of acylation agent introduced}}{\text{number of moles of acylated aromatic compound formed}} \ \%$$

EXAMPLE 1

In this example, a β zeolite with a "global Si/Al" ratio of 25.2 was prepared.

The starting zeolite was a zeolite with a "global Si/Al" ratio of 12.5 sold by PQ Zeolites, reference number CVB 811BL25.

50 g of the β zeolite was suspended in 250 ml of a 0.5N nitric acid solution in a cooled flask.

The mixture was heated under reflux for 3 hours.

The zeolite was then washed with distilled water until the pH of the washing water was neutral.

The "global Si/Al" ratio of the prepared β zeolite, determined by X ray fluorescence, was 25.2.

EXAMPLE 2

In this example a β zeolite with a "global Si/Al" ratio of 43 was prepared.

50 g of the β zeolite defined in Example 1 with a "global Si/Al" ratio of 12.5 was suspended in 250 ml of a 1.3N nitric acid solution in a cooled flask.

The mixture was heated under reflux for 4 hours.

The zeolite was then washed with distilled water until the pH of the washing water was neutral.

The "global Si/Al" ratio of the prepared β zeolite, determined by X ray fluorescence, was 43.

EXAMPLE 3

This example concerned the use of the zeolite prepared in Example 1 for the acetylation of anisole.

13 ml of β zeolite (i.e., about 5 g) was introduced in powder form into a tube reactor heated by a double envelope.

The double envelope was heated to 100° C. and an HPLC pump was used to introduce a mixture of anisole and acetic anhydride into the bottom of the reactor, in a molar ratio of 2 and at a flow rate of 0.2 ml/min.

The reaction mixture was continuously extracted by overflowing.

The reaction yield was followed over time by taking aliquots which were analysed by gas chromatography.

The results obtained were as follows:

TABLE (I)

| Time (hours) | $RR_{AA}$ (%) |
|---|---|
| 0 | 85 |
| 1 | 98 |
| 6 | 100 |
| 22 | 90 |
| 25 | 89 |
| 30 | 85 |

After 30 hours of operation, 306 g of acetoanisole was isolated. Under these conditions the productivity, expressed in grams of acetoanisole per gram of catalyst per hour, was 2.04 g for a period of 30 hours.

EXAMPLE 4

This example concerned the use of the zeolite prepared in Example 2 for the acetylation of anisole.

13 ml of β zeolite (i.e., about 5 g) was introduced in powder form into a tube reactor heated by a double envelope.

The double envelope was heated to 100° C. and an HPLC pump was used to introduce a mixture of anisole and acetic anhydride into the bottom of the reactor, in a molar ratio of 2 and at a flow rate of 0.2 ml/min.

The reaction mixture was continuously extracted by overflowing.

The reaction yield was followed over time by taking aliquots which were analysed by gas chromatography.

The results obtained were as follows:

TABLE (II)

| Time (hours) | $RR_{AA}$ (%) |
|---|---|
| 0 | 51.3 |
| 6 | 93.5 |
| 23 | 78 |
| 30 | 75 |

After 30 hours of operation, 229 g of acetoanisole was isolated. Under these conditions, the productivity was 1.52 g for a period of 30 hours.

EXAMPLE 5

This comparative test used a zeolite described by Prins et al., (cited above) for the acetylation of anisole.

The zeolite used was a zeolite with a "global Si/Al" ratio of 12.5 sold by PQ Zeolites, reference number CVB 811BL25.

13ml of β zeolite (i.e., about 5.1 g) was introduced in powder form into a tube reactor heated by a double envelope.

The double envelope was heated to 100° C. and an HPLC pump was used to introduce a mixture of anisole and acetic anhydride into the bottom of the reactor, in a molar ratio of 2 at a flow rate of 0.2 ml/min.

The reaction mixture was continuously extracted by overflowing.

The reaction yield was followed over time by taking aliquots which were analysed by gas chromatography.

TABLE (III)

| Time (hours) | $RR_{AA}$ (%) |
|---|---|
| 0 | 60 |
| 1 | 54 |
| 2.5 | 54 |
| 3.5 | 51.6 |
| 4.5 | 53.4 |
| 21.25 | 41 |
| 26.75 | 41 |
| 28.75 | 38 |

After 30 hours of operation, 83 g of acetoanisole was isolated. Under these conditions, the productivity was 0.54 g for a period of 30 hours.

EXAMPLE 6

Acetylation of Veratrol 119.5 g of veratrol (0.86 mole), 43.6 g of acetic anhydride (0.43 mole) and 11.2 g of the catalyst prepared in Example 1 were charged into a closed 300 ml reactor.

The reactor was heated to 90° C.

After 7 hours, the reaction mixture was filtered then analysed by gas chromatography.

The acetoveratrol (3,4-dimethoxyacetophenone) yield obtained was: $RR_{AA}=82\%$.

EXAMPLE 7

Acetylation of Veratrol

Veratrol was acetylated under the operating conditions of Example 6 using the catalyst of Example 2.

After 7 hours, the acetoveratrol yield obtained was: $RR_{AA}=78\%$.

EXAMPLE 8

Acetylation of 1.2-Methylenedioxybenzene 1,2-methylenedioxybenzene was acetylated under the conditions described in Example 6 using the catalyst described in Example 1.

119 g of 1,2-methylenedioxybenzene (0.97 mole), 50.4 g of acetic anhydride (0.49 mole) and 12.2 g of catalyst were loaded.

After 7 hours, the yield of para-acetylated product was: $RR_{AA}=61\%$.

EXAMPLE 9

In this comparative test, 1,2-methylenedioxybenzene was acetylated as in Example 8, but using the zeolite described by Prins et. al. (cited above)

After 7 hours, the yield of para-acetylated product was: $RR_{AA}=37\%$.

What is claimed is:

1. A process for the acylation of an aromatic ether comprising reacting said ether with an acylation agent selected from the group consisting of linear or branched aliphatic carboxylic acid halides, linear or branched aliphatic carboxylic acid anhydrides saturated or unsaturated cycloaliphatic carboxylic acid halides, and saturated or unsaturated cycloaliphatic carboxylic acid anhydrides in the presence of a zeolitic catalyst, said acylation reaction being carried out in the presence of an effective quantity of a catalyst comprising a beta zeolite with an atomic ratio denoted "global $Si/Me^1$" between the number of atoms of the element silicon and the number of atoms of every trivalent element $Me^1$ contained in the zeolite of not less than 15.

2. A process according to claim 1, wherein the atomic ratio is in the range 15 to 55.

3. A process according to claim 2, wherein the atomic ratio is in the range 18 to 35.

4. A process according to claim 1, wherein the aromatic ether has general formula (I):

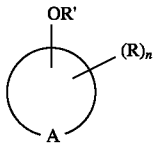

(I)

wherein:

A represents the residue of a cycle forming all or a portion of a monocyclic or polycyclic aromatic carbocyclic system containing at least one OR' group, A optionally carrying one or more substituents;

R represents one or more identical or different substituents;

R' represents a saturated or unsaturated hydrocarbon radical containing 1 to 24 carbon atoms, a linear or branched acyclic aliphatic radical; a monocyclic or polycyclic, saturated, unsaturated or aromatic cycloaliphatic radical; or a saturated or unsaturated, linear or branched aliphatic radical carrying a cyclic substitutent;

R' and R optionally forming a cycle optionally containing a further heteroatom; and n is a number less than or equal to 4.

5. A process according to claim 4, wherein R' represents:
- a saturated or unsaturated, linear or branched acyclic aliphatic radical, containing 1 to 12 carbon atoms, the hydrocarbon chain being optionally interrupted by a heteroatom, a functional group or carrying a substitutent;
- a saturated or unsaturated, linear or branched acyclic aliphatic radical carrying a cyclic substitutent optionally substituted, said acyclic radical being bonded to the cycle by a valence bond, a heteroatom or a functional group;
- a carbocyclic radical which may be saturated or contain 1 or 2 unsaturations in the cycle, containing 3 to 8 carbon atoms in the cycle; said cycle being optionally substituted; and
- an aromatic carbocyclic radical containing at least 4 carbon atoms, said carbocyclic radical being optionally substituted.

6. A process according to claim 4, wherein R' represents a methyl, ethyl or phenyl radical, R and R' optionally forming a dioxymethylene or dioxyethylene radical.

7. A process according to claim 4, wherein A represents the residue of a monocyclic aromatic carbocyclic compound containing at least 4 carbon atoms or the residue of a polycyclic carbocyclic compound, A optionally carrying one or more substituents on the aromatic residue.

8. A process according to claim 1, wherein the aromatic ether has formula (Ia):

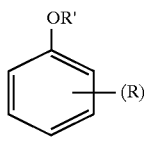

(Ia)

wherein:
n is a number less than or equal to 4;
radical R' represents a linear or branched alkyl radical containing 1 to 6 carbon atoms or a phenyl radical;
radical(s) R is selected from the group consisting of:
- a linear or branched alkyl radical containing 1 to 6 carbon atoms a linear or branched alkenyl radical containing 2 to 6 carbon atoms;
- a cyclohexyl or benzyl radical;
- a linear or branched alkoxy radical containing 1 to 6 carbon atoms; and
- a radical with formula selected from the group consisting of:
  —$R_1$—OH,
  $R_1$—$COOR_2$,
  —$R_1$—CHO,
  —$R_1$—$NO_2$,
  —$R_1$—CN,
  —$R_1$—N—$(R_2)_2$,
  —$R_1$—CO—N—$(R_2)_2$,
  —$R_1$—X,
  —$R_1$—$CF_3$,
  wherein $R_1$ represents a valence bond or a saturated or unsaturated, linear or branched divalent hydrocarbon radical containing 1 to 6 carbon atoms; $R_2$ represents a hydrogen atom or a linear or branched alkyl radical containing 1 to 6 carbon atoms; and X represents a halogen atom; and
radicals R' and R and the 2 successive atoms of the benzene ring optionally forming between them a cycle containing 5 to 7 carbon atoms optionally containing a further heteroatom.

9. A process according to claim 8, wherein n is greater than or equal to 1, radicals R and R' and the 2 successive atoms of the benzene ring can be bonded together by an alkylene, alkenylene or alkenylidene radical containing 2 to 4 carbon atoms to form a saturated, unsaturated or aromatic heterocycle containing 5 to 7 carbon atoms in which one or more carbon atoms can be optionally replaced by a heteroatom, the radicals OR' and R optionally forming a dioxymethylene or dioxyethylene radical.

10. A process according to claim 4, wherein:
n i 0 or 1;
R' represents a linear or branched alkyl radical containing 1 to 6 carbon atoms or a phenyl radical;
R represents a linear or branched alkoxy radical containing 1 to 4 carbon atoms; and
radicals OR' and R optionally forming a dioxymethylene or dioxyethylene radical.

11. A process according to claim 8, wherein:
n is 0 or 1;
R40 represents a linear or branched alkyl radical containing 1 to 6 carbon atoms or a phenyl radical;
R represents a linear or branched alkoxy radical containing 1 to 4 carbon atoms; and
radicals OR' and R optionally form a dioxymethylene or dioxyethylene radical.

12. A process according to claim 4, wherein n equals 0; radical R' represents ethyl, propyl, isopropyl, butyl, isobutyl, sec-butyl, tert-butyl or a phenyl radical.

13. A process according to claim 4, wherein said aromatic ether is anisole.

14. A process according to claim 8, wherein n equals 0; radical R' represents ethyl, propyl, isopropyl, butyl, isobutyl, sec-butyl, tert-butyl or a phenyl radical.

15. A process according to claim 8, wherein said aromatic ether is anisole.

16. A process according to claim 1, wherein the acylation agent has formula (II):

(II)

wherein:
$R_3$ represents:
- a saturated or unsaturated, linear or branched aliphatic radical containing 1 to 24 carbon atoms; or a saturated or unsaturated, monocyclic or polycyclic cycloaliphatic radical containing 3 to 12 carbon atoms;

X' is selected from the group consisting of:
- a halogen atom;
- a —O—CO—$R_4$ radical wherein $R_4$, which may be identical or different to $R_3$, has the same meaning as $R_3$; $R_3$ and $R_4$ optionally forming together a saturated or unsaturated, linear or branched aliphatic radical containing at least 2 carbon atoms.

17. A process according to claim 16, wherein X' represents a chlorine atom and $R_3$ represents a linear or branched alkyl radical containing 1 to 12 carbon atoms, the hydrocarbon chain being optionally interrupted by a heteroatom or by a functional group or optionally carrying halogen atoms; or X' represents a —O—CO—$R_4$ radical, wherein $R_3$ and $R_4$ are identical and represent an alkyl radical containing 1 to 4 carbon atoms optionally carrying halogen atoms.

18. A process according to claim 16, wherein the acylation agent is selected from the group consisting of:

acetic anhydride;
propanoic anhydride;
isobutyric anhydride;
trifluoroacetic anhydride;
monochloroacetyl anhydride;
dichloroacetyl anhydride;
acetyl chloride;
monochloroacetyl chloride;
dichloroacetyl chloride;
propanoyl chloride;
isobutanoyl chloride;
pivaloyl chloride; and
crotonyl chloride.

19. A process according to claim 1, wherein the catalyst is a β zeolite having, in its dehydrated state, a chemical composition corresponding to the following empirical formula:

$$1-x)H_2O, x[(Me^2)_2O],[(Me^1)_2O_3], 2nSiO_2$$

wherein:
  $Me^1$ represents an element with a degree of oxidation of +3;
  $Me^2$ represents a alkali metal selected from the group of elements from column 1a and mixtures thereof;
  n, equal to the "global $Si/Me^1$" atomic ratio is in the range 15 to 55; and
  x, equal to the $Me^2/Me^1$ atomic ratio, between the number of atoms of alkali metal $Me^2$ and the number of atoms of every trivalent element $Me^1$ in the zeolite, is in the range 0 to 0.2.

20. A process according to claim 19, wherein $Me^1$ represents aluminium and $Me^2$ represents sodium or potassium, or a mixture of sodium and potassium.

21. A process according to claim 20, wherein the β zeolite undergoes dealuminising treatment so that the $Si/Me^1$ atomic ratio is in the range 0.005 to 0.1.

22. A process according to claim 21, wherein the dealuminising treatment comprises one of the following steps: calcining in the presence of vapour, calcining in the presence of steam followed by attack with mineral acids, dealuminising using reactants selected from the group consisting of silicon tetrachloride ($SiCl_4$), ammonium hexafluorosilicate (($NH_4)_2SiF_6$), ethylenediaminetetracetic acid (EDTA), and mono or disodium form of EDTA; and direct acid attack using solutions of mineral acids or organic acids.

23. A process according to claim 1, wherein the zeolite is used alone or mixed with a mineral matrix which is selected from the group consisting of metal oxides, aluminium oxides, silicon oxides, zirconium oxides, clays, kaolin, talc and montmorillonite.

24. A process according to claim 1, further comprising the use of an organic solvent selected from the group consisting of:
  aliphatic, cycloaliphatic or aromatic hydrocarbons;
  aliphatic or aromatic halogenated hydrocarbons;
  aliphatic, cycloaliphatic or aromatic ether-oxides;
  linear or cyclic carboxamides;
  dimethylsulphoxide (DMSO);
  cyclic or non cyclic sulphones;
  hexamethylphosphotriamide (HMPT); and
  cyclic or non cyclic tetrasubstituted ureas.

25. A process according to claim 1; wherein the ratio between the number of moles of aromatic ether and the number of moles of acylation agent is between 0.1 and 20.

26. A process according to claim 1, wherein the quantity of catalyst represents 0.01% to 50% by weight of the aromatic ether employed.

27. A process according to claim 1, wherein the temperature at which the acylation reaction is carried out is between 20° C. and 300° C.

* * * * *